US009817007B2

(12) United States Patent
Perez

(10) Patent No.: US 9,817,007 B2
(45) Date of Patent: Nov. 14, 2017

(54) METHOD AND APPARATUS FOR REAL-TIME DETECTION OF HUMAN CANNABINOID INTOXICATION

(71) Applicant: John Scott Perez, Tampa, FL (US)

(72) Inventor: John Scott Perez, Tampa, FL (US)

(*) Notice: Subject to any disclaimer, the term of this patent is extended or adjusted under 35 U.S.C. 154(b) by 100 days.

(21) Appl. No.: 14/636,416

(22) Filed: Mar. 3, 2015

(65) Prior Publication Data
US 2015/0253344 A1 Sep. 10, 2015

Related U.S. Application Data

(60) Provisional application No. 61/966,933, filed on Mar. 5, 2014.

(51) Int. Cl.
*G01N 31/16* (2006.01)
*G01N 33/94* (2006.01)

(52) U.S. Cl.
CPC .................. *G01N 33/948* (2013.01)

(58) Field of Classification Search
USPC ................ 436/55; 422/68.1, 547, 554, 502; 435/40.52
See application file for complete search history.

(56) References Cited

U.S. PATENT DOCUMENTS

| 5,817,766 A * | 10/1998 | Hui ...................... C07D 311/58 422/412 |
| 6,673,533 B1 * | 1/2004 | Wohlstadter .......... B01L 3/5027 204/400 |
| 7,700,305 B2 * | 4/2010 | Toranto .................... C12Q 1/26 422/412 |
| 8,417,465 B2 * | 4/2013 | Prabhakarpandian G01N 33/5029 702/19 |
| 2009/0004058 A1 * | 1/2009 | Liang .................. A61B 10/0096 422/68.1 |
| 2015/0268257 A1 * | 9/2015 | Klaus ................... G01N 33/558 435/7.2 |

* cited by examiner

*Primary Examiner* — Nina Bhat
(74) *Attorney, Agent, or Firm* — John L. Doughty

(57) ABSTRACT

A method for quantifying the intoxicating affect of natural and synthetic Cannabinoids on Humans. The method includes the capacity to measure a human's psychoactive intoxication as a function of Cannabinoid-Mediated Depolarization-Induced Suppression of Inhibition (C-DISI) relative to the Cannabinoid Receptors found in the Human brain. A Method incorporating the ability to also quantify the affects of Cannabinoids on the various Cannabinoid Receptors found in the Human body. Neurons are used as transistors in a solid state electronic configuration with an apparatus to measure the toxicity of a given aqueous solution comprised of one or more Cannabinoid analytes. Said method incorporates a novel recycling process affiliated with analyte acquisition & testing.

14 Claims, 7 Drawing Sheets

METHOD AND APPARATUS FOR REAL-TIME DETECTION OF HUMAN CANNABINOID INTOXICATION

BACKGROUND INFORMATION

Consumption of Cannabinoid molecules by humans results in intoxication. Cannabinoid intoxication in humans has been determined to be a function of a mechanism known as Cannabinoid-Mediated Depolarization Induced Suppression of Inhibition (C-DISI). C-DISI is an electrically measureable process of decoupling a neural circuit in the human brain. C-DISI occurs when a psycho active cannabinoid molecule binds to a neural Glycolipid-Protein receptor in the human brain known as the Cannabinoid Receptor type 1 (CB1). The C-DISI outcome of the cannabinoid binding results in a voltage drop from a positively stimulated voltage to −30 to 0 mV.

Marijuana naturally contains psychoactive cannabinoids. There are also a number of synthetic cannabinoid molecules that behave similarly to Marijuana. Today Marijuana has become legalized for medical consumption in 23 of the United States. Two states have legalized the consumption of Marijuana for recreational use. There are no clearly defined regulations on synthetic cannabinoids for use in the United States. Many political groups have projected that the legalization of cannabinoids for medical and recreational use will occur in the United States at the Federal Regulatory level in the near future. These movements have created a problem for the ability of law enforcement, the military, and companies to cheaply test humans for intoxication by cannabinoids in real-time to determine intoxication as is performed in the case of alcohol consumption. Testing sensitivity below 25 ng/ml of Delta-9 Tetrahydracannibanoid for portable saliva testing has yet to be achieved. The capacity to test both blood and saliva at sub 5 ng/ml and 25 ng/ml levels respectively with a portable system has not been achieved.

BRIEF DESCRIPTION OF THE DRAWINGS

Various exemplary embodiments are illustrated by way of example, and not by way of limitation, in the figures accompanying drawings in which like reference numerals refer to similar elements and in which.

DETAILED DESCRIPTION OF PREFERRED EMBODIMENTS

The following detailed description refers to the accompanying drawings. The same reference numbers in different drawings may identify the same or similar elements. The detailed description does not limit the invention.

Figure 1:
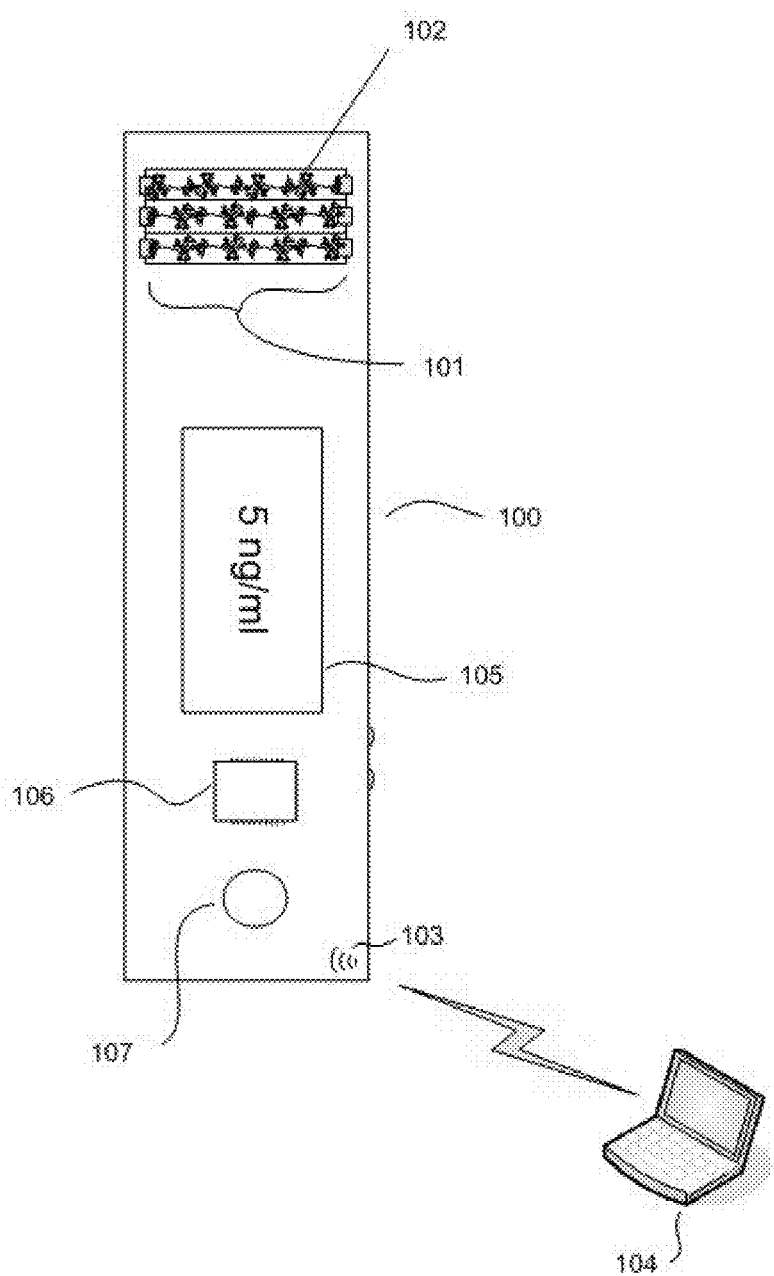
FIG. 1 is an illustration of an embodiment that can be used for detection of cannabinoids.

Systems and methods described herein describe the cannabinoid detection device (CDD) 100 of FIG. 1. The CDD is one capable of sending −70 to +90 mV electrical voltage pulses across neural circuits 102 located on a removable chip 101 and simultaneously measuring the conductivity of the voltage potential of said circuit 102. The device may be interfaced to radio communications circuits such as Bluetooth, etc. 103 for the purpose of transmitting collected data to other electronic devices, such as a computer or smart device 104. The values corresponding to the CDD test are displayed in terms of toxicity on an analog display 105. The CDD uses a typical microprocessor circuit 106 for the purpose of calibration and analytics. The CDD is powered by a battery 107.

Figure 2:
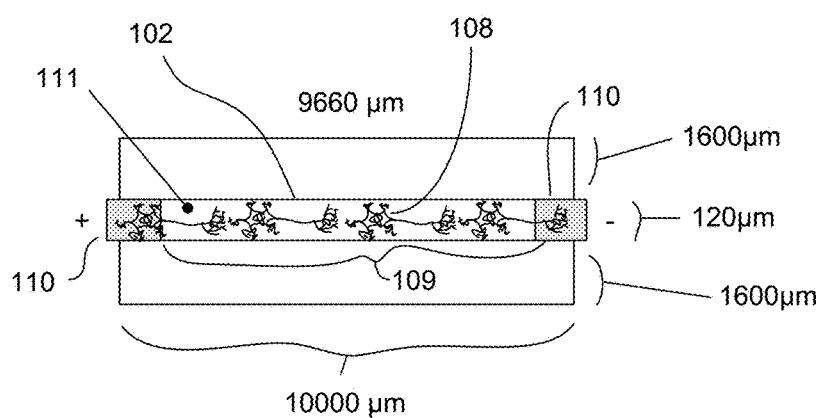
FIG. 2 is a diagram of an electrical circuit that can be used to measure Cannabinoid-Mediated Depolarization Induced Suppression of Inhibition (C-DISI).

FIG. 2 shows the neural circuit design 102 for a chip that can be used to test for C-DISI. As shown the neurons used in the circuit are human glial neuron cell lines of brain origin that have been established for research using traditional best practices & accepted protocols 108. The glial neural cell lines are cultured on the circuit junction 109 to from the neural circuit 108 between the electrodes 110 of the chip. Sterile methods are used to culture the human neural cells across the gap 109 between the two electrodes 110 using nutrient medium 111. The neural circuit is not limited to glial neural cells with the CB1 G-Protein receptors. The neural circuit 102 can be constructed from other human cells 108 containing the CB1 or the Cannabinoid G-Protein Receptor 2 (CB2) for the purpose of illustrating C-DISI toxicity in those neural cell lines.

The voltage potential across the two electrodes 110 will be a positive voltage from 1-90 mV prior to the introduction of cannabinoids to the growth medium. Introduction of cannabinoids to the neural circuit 102 will result in the reduction of the voltage potential between the two electrodes 110 to −30 to 0 mV for a period of time. The neural circuit 102 is not cannabinoid molecule specific, and is capable of measuring voltage potential signatures of multiple cannabinoid molecules. The delectability of the CB1 receptor is the same for psychoactive cannabinoids found in the naturally occurring Marijuana plant as it is for the synthetic cannabinoids that have been well documented in the literature as psychoactive. It is completely normal for cannabinoid molecules to form isomers and be in mixtures thereof during human consumption. There are many CB1 receptors on the synaptic clefts of the human neural glial cell junctions. The ability of the CB1 receptor to bind multiple cannabinoid molecule types with the same specified sensitivity as the human brain of a human allows for diagnostic testing that is real world analogous to what occurs when a human consumes cannabinoids.

Figure 3A:
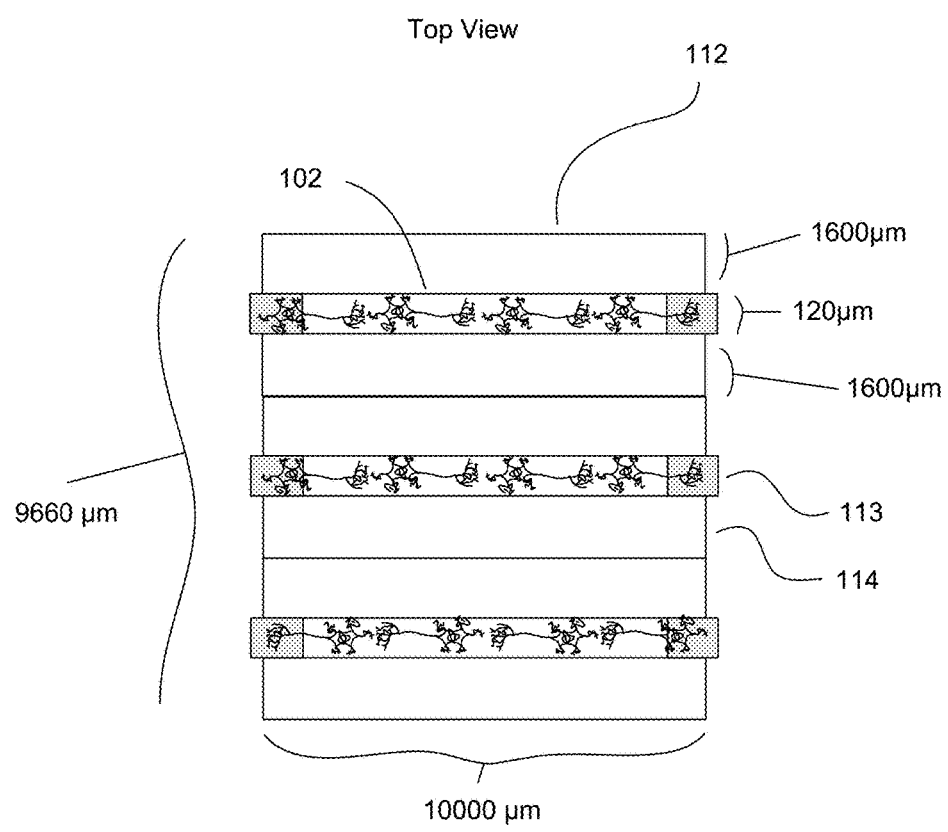
FIG. 3A is a top view diagram of a chip that houses multiple electrical circuits capable of measuring C-DISI.

FIG. 3A illustrates the top view dimensions of the chip 112 used to house the neural circuit 102 across a 120 μm channel 113 separated by 1600 μm angled vertical declines 114 that guide aqueous solution to the neural circuit 102 so that shaking or adding of aqueous solution always returns to the neural circuit 102. The horizontal length of the chip 112 is 10,000 μm and the horizontal depth is 9660 μm. The chip's function is not limited to size, but its function is based on the geometric concepts used to house the neural circuit. Said chip 112 houses 3 neural circuits but is not limited by size or circuit number. Other embodiments could house 3 or more neural circuits to accommodate more sophisticated CDD equipment.

Figure 3B:
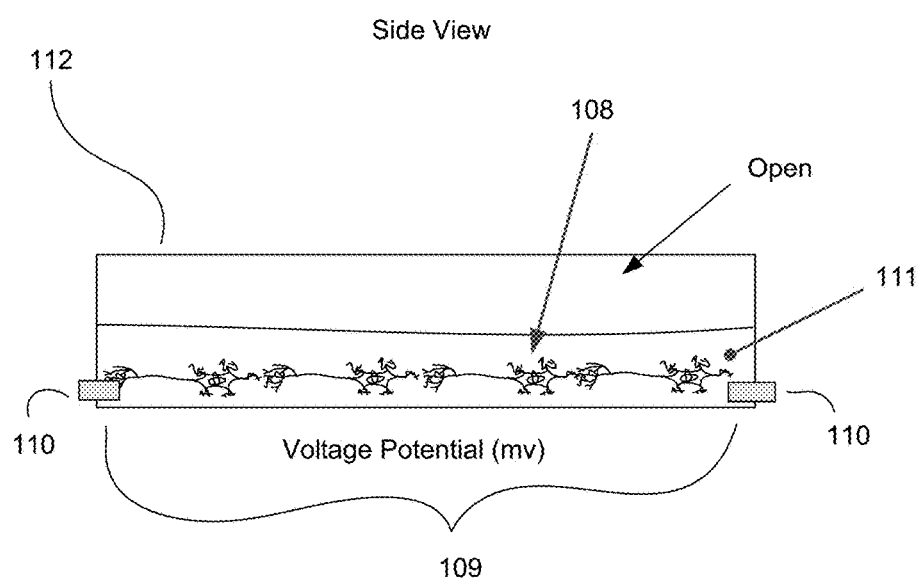
FIG. 3B is a side view diagram of a chip that houses multiple electrical circuits capable of measuring C-DISI.

FIG. 3B shows the horizontal length side view of the chip 112 housing nutrient medium 111 across electrodes 110.

Figure 3C:
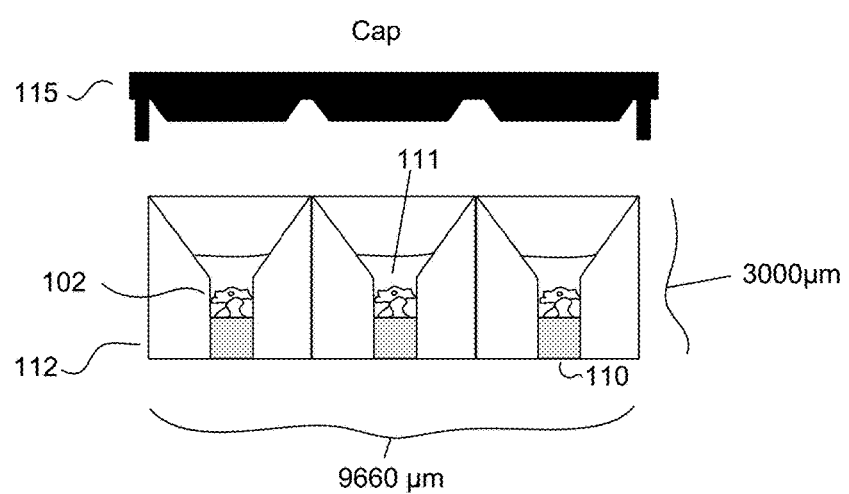
FIG. 3C is a turned side view diagram of a chip that houses multiple electrical circuits capable of measuring C-DISI.

FIG. 3C shows the horizontal depth side view of the chip 112 with the clear cap 115 capable of sealing the circuit reservoirs 102 from the top.

The CB1 receptor by structural design binds each type of cannabinoid molecule with specific affinity. The affinity has been well documented in the professional literature as a function of toxicity. The binding affinity of the cannabinoid mixture will have a specific time based C-DISI voltage drop signature and recovery that is completely measureable by said microprocessor 106. The cannabinoid toxicity values for saliva, blood, and brain tissue have been worked out by researchers. Standards representing the diluted and concentrated contents of cannabinoids relative to the known research values determined can be created for the purpose of calibrating the CDD and forming a linear regression plot.

Figure 4:
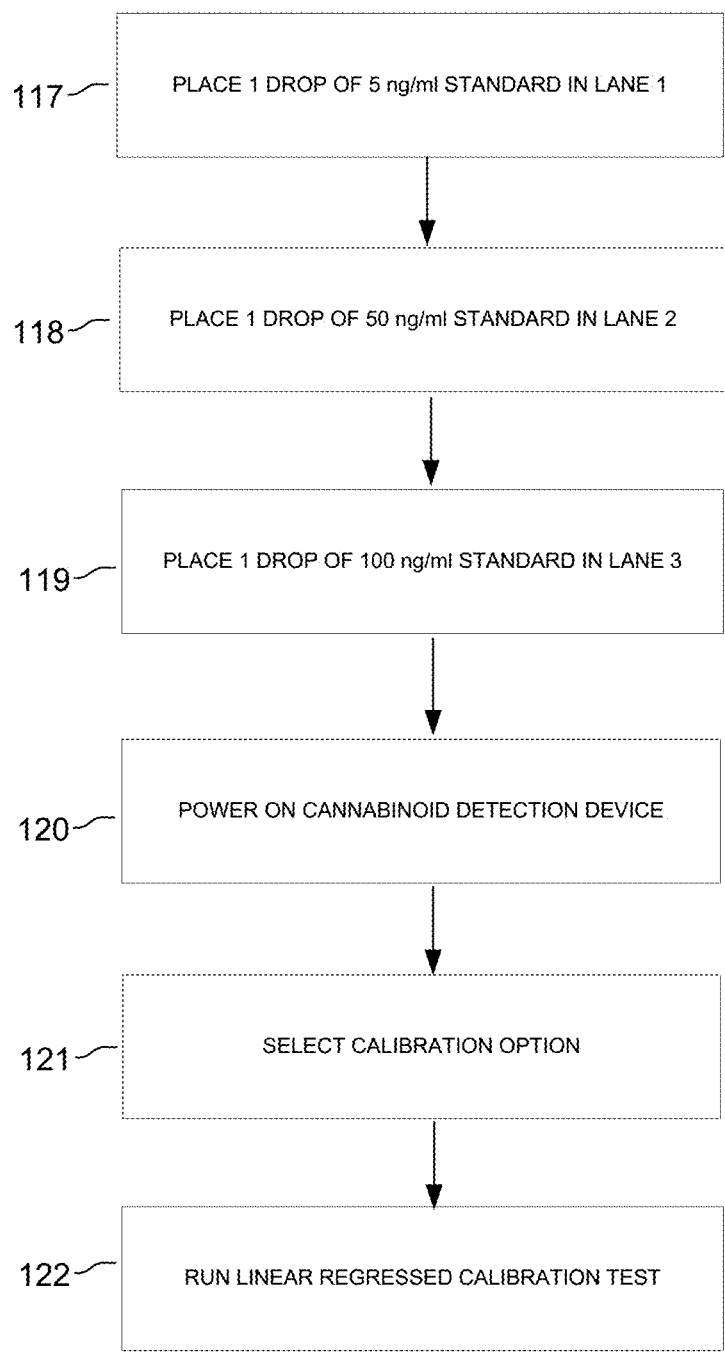
FIG. 4 is a flow diagram of an exemplary process associated with device calibration.

FIG. 4 illustrates the process for CDD calibration using linear regression. The test is performed by first placing 1 drop of 5 ng/ml of THC standard in circuit lane #1 117, followed by placing 1 drop of 50 ng/ml of THC standard in circuit lane #2 118. Lastly, 1 drop of 100 ng/ml of THC standard is placed in lane #3 119. The CDD is powered on 120. The calibration option is selected 121. The linear regression calibration process is run 122.

Figure 5:
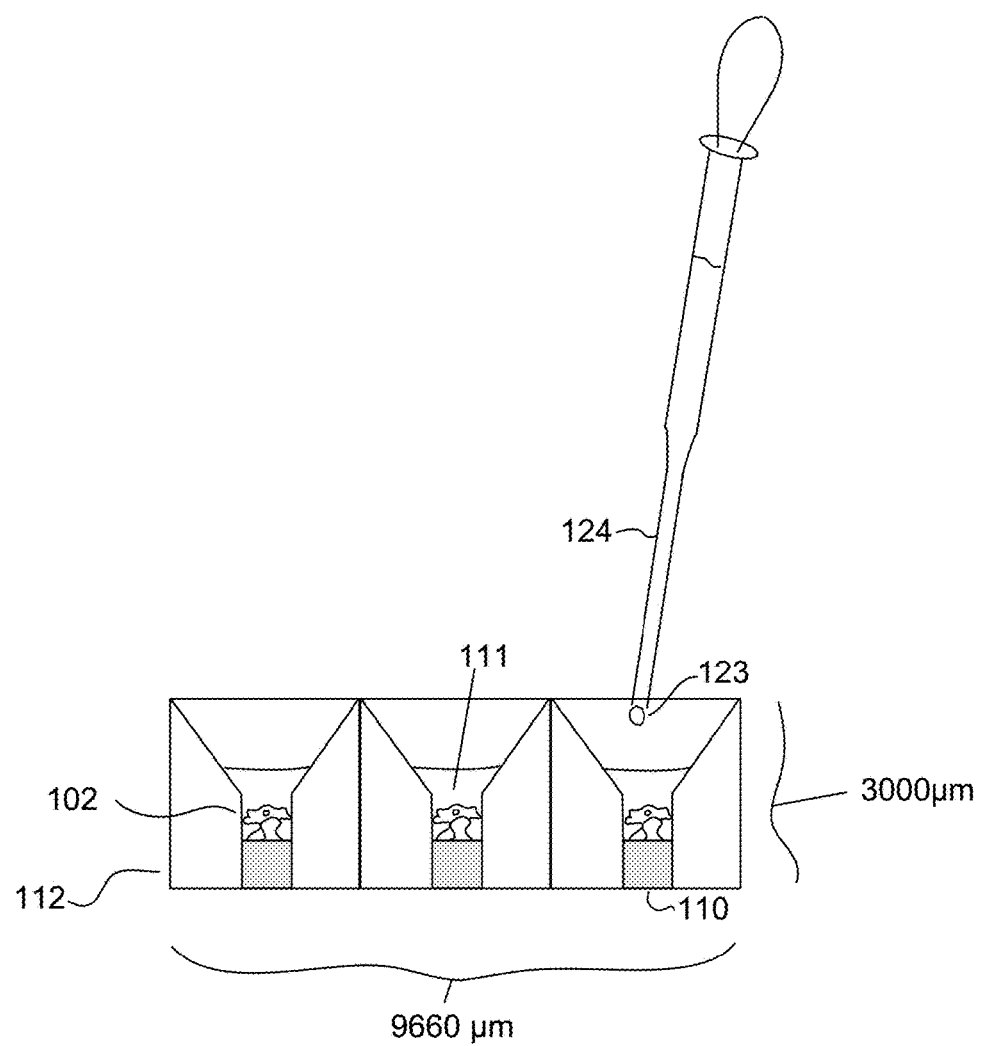
FIG. 5 is an illustration of the testing analysis addition of aqueous analyte relative to a chip housing an C-DISI circuit used in a device for human subject testing.

FIG. 5 illustrates the CDD test method in which a dropper 124 is used to add 1 drop of the aqueous saliva sample from the human subject 123. The equivalent of >5 ng/ml of Delta 9 Tetrahydracannabinol is considered toxic in the blood of human beings. Similarly >25 ng/ml of Delta 9 Tetrahydracannabinol is considered toxic in the saliva of a human being within the 4-6 hr time frame from last consumption. The toxicity of the cannabinoid molecule type affects the CB1 receptors in the brain. Leveraging the CB1 receptors in the CDD allows for real-time field testing of humans without the use of very sophisticated and bulky laboratory equipment. It allows for the CDD to be used for testing either blood or saliva at the lowest possible concentrations capable of producing C-DISI in human glial neurons. This results in extreme accuracy with respect to cannabinoid selectivity versus traditional analytical chemical methods. Traditional laboratory equipment requires years of training and subject matter expertise that the average person may not have. The ability to provide a simple test in terms of scale allows people to test suspected individuals who may have consumed cannabinoids and determine with great accuracy the presence and level of cannabinoid impairment.

The CDD chip can be removed and cold stored and sent to a laboratory for more expensive analytical analysis and validation in the event that the CDD test has determined toxicity. Upon completion of use of the chip 112 the chip itself can be cleaned using traditional surfactant washing methods and re sterilized with an autoclave. The chip 112 can then be re-used by the consumer base to keep costs down. This introduces a novel recycling path to the test process that keeps the process down for the target consumer base thus making the cost of testing more practical.

What is claimed is:

1. A device for detecting a cannabinoid concentration present in an aqueous solution in real-time, wherein the device comprises: a chip having at least one neural circuit for measuring Cannabinoid-Mediated Depolarization-Induced Suppression of Inhibition wherein the device further comprises a processor that is configured to identify human toxicity across a range of concentrations of cannabinoids in the aqueous solution by evaluating a C-DISI voltage drop-and-recovery signature that occurs in the neural circuit in response to an application of the aqueous solution to the neural circuit.

2. The device of claim 1, wherein the device is a hand-held unit.

3. The device of claim 1, further comprising a wireless transceiver for transmitting data corresponding to the cannabinoid concentration in the aqueous solution.

4. The device of claim 1, wherein the neural circuit is a human neural circuit for conducting electrical current.

5. The device of claim 4, wherein the neural circuit includes at least one human cannabinoid receptor for binding more than one type of cannabinoid molecule.

6. The device of claim 4, wherein conductivity of the neural circuit changes differently for different types of natural and synthetic cannabinoid molecules in the aqueous solution sample as a function of Cannabinoid-Mediated Depolarization-Induced Suppression of Inhibition.

7. The device of claim 1, wherein the chip can withstand cleaning and re-use.

8. The device of claim 1, further comprising a cap that fits over the at least one neural circuit.

9. The device in claim 4, wherein conductivity of the neural circuit changes according to Cannabinoid-Mediated Depolarization-Induced Suppression of Inhibition that results from applying a sample containing one or more cannabinoids to the aqueous solution that buffers the neural circuit and wherein changes in conductivity of the neural circuit substantially correlate with sensitivity of the human brain's neurons to cannabinoid toxicity.

10. The device of claim 1 wherein the concentration range extends from below 5 ng/ml for blood.

11. The device of claim 1 wherein the concentration range extends from below 25 ng/ml for saliva.

12. The device of claim 1 wherein the at least one neural circuit is disposed between a first electrode and a second electrode, wherein the device applies an electrode potential between the first electrode and the second electrode, and wherein the electrode potential changes according to the cannabinoid toxicity when a sample containing the cannabinoid is applied to the aqueous solution that buffers the neural circuit.

13. The device of claim 1 wherein a specific time-based C-DISI voltage drop-and-recovery signature that occurs in the neural circuit in response to an application of a sample of a specific cannabinoid molecule to the aqueous solution that buffers the neural circuit corresponds to a specific binding affinity of the specific cannabinoid molecule and the neural circuit.

14. The device of claim 1 wherein a specific C-DISI voltage drop-and-recovery signature that occurs in the neural circuit in response to an application of a mixture of cannabinoid molecules to the aqueous solution that buffers the neural circuit corresponds to a cannabinoid toxicity level associated with multiple binding affinities.

* * * * *